United States Patent [19]

Grivsky

[11] 4,041,071
[45] Aug. 9, 1977

[54] ANTI-CONVULSANT CINNAMIDE COMPOUNDS

[75] Inventor: Eugene M. Grivsky, Chapel Hill, N.C.

[73] Assignee: Burroughs Wellcome Co., Research Triangle Park, N.C.

[21] Appl. No.: 596,653

[22] Filed: July 17, 1975

[30] Foreign Application Priority Data

Aug. 9, 1974 United Kingdom .............. 35279/74

[51] Int. Cl.$^2$ ................. C07C 103/22; C07C 103/76; A61K 31/165
[52] U.S. Cl. .......................... 260/558 R; 260/476 R; 260/544 D; 260/558 D; 424/324
[58] Field of Search ....................... 260/558 D, 558 R

[56] References Cited

U.S. PATENT DOCUMENTS

| 3,488,749 | 1/1970 | Loev et al. ............. | 424/324 |
| 3,590,041 | 6/1971 | Kleemann et al. ............. | 260/240 |
| 3,780,102 | 12/1973 | Bayssat et al. ............. | 260/558 D X |

FOREIGN PATENT DOCUMENTS

| 516,554 | 1/1972 | Switzerland |
| 1,128,120 | 9/1968 | United Kingdom |
| 1,171,042 | 11/1969 | United Kingdom |
| 1,128,142 | 4/1971 | United Kingdom |
| 1,131,727 | 10/1968 | United Kingdom |
| 1,396,941 | 6/1975 | United Kingdom |
| 1,396,942 | 6/1975 | United Kingdom |

OTHER PUBLICATIONS

Claisse et al., CA 72:21696h (1970).
Smith, Kline and French Lab., CA 70:37497p (1969).
Pagini et al., CA 79:28246q (1973).
Pagini et al., CA 79:28247r (1973) - *Farmaco, Ed. Sci.* 1973, 28(3), 231–242.
Chim. Ther. 2 (5), pp. 354–365 (1971).

*Primary Examiner*—Daniel E. Wyman
*Assistant Examiner*—Thomas A. Waltz
*Attorney, Agent, or Firm*—Donald Brown

[57] ABSTRACT

Cinnamamide compounds of the formula

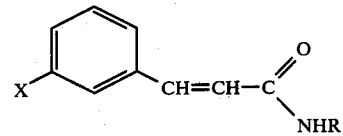

where X is chloro, bromo or iodo and R is hydrogen or alkyl of 1 to 3 carbons as pharmaceuticals which are useful in the treatment or prophylaxis for convulsions.

6 Claims, No Drawings

ANTI-CONVULSANT CINNAMIDE COMPOUNDS

This invention is concerned with new chemicals which have valuable pharmacological properties. In particular, the invention concerns novel cinnamamides, their synthesis, pharmaceutical preparations containing them, and their use in medicine.

It has been found that the cinnamamides of formula (I), as defined below, have anti-convulsant activity in mammals as is shown by their effects upon mice when administered to them in established pharmacological tests. These tests are:

1. Maximal Electroshock Test (MES) in mice, a method described by Woodbury and Davenport, Arch. int. Pharmacodyn. Ther. 92. P. 97–107 (1952).
2. Metrazol Seizure Test (MET) in mice, a method described by Swinyard, Brown and Goodman, J. Pharmacol. Exp. Therap. 106, 319–330 (1952).

In formula (I)

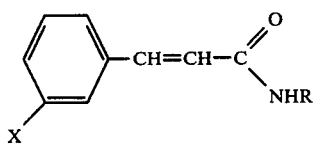

(I)

X is chlorine, bromine or iodine, and R is hydrogen or alkyl having 1 to 3 carbon atoms. The trans configuration of the compounds of formula (I) is preferred; and the compound wherein R is ethyl and X is bromine in the trans configuration has outstanding anti-convulsant activity in both pharmacological tests described above. Other examples of compounds within the scope of formula (I) include:

trans 3-Bromo-N-methylcinnamamide
trans 3-Bromo-N-n-propylcinnamamide
trans 3-Bromo-N-isopropylcinnamamide
trans 3-Chloro-N-methylcinnamamide
trans 3-Chloro-N-ethylcinnamamide
trans 3-Chloro-N-n-propylcinnamamide
trans 3-iodocinnamamide, trans 3-iodo-N-isopropylcinnamamide The compounds of formula (I) may be made by any method known for the synthesis of cinnamamides of analogous structure. For example they may be prepared by the acylation of an amine $RNH_2$ (wherein R is hydrogen or alkyl having 1–3 carbon atoms) by the corresponding acid of formula (II): m-X-PhCH = $CHCO_2H$ (wherein X has the meaning given for formula (I)) or a reactive derivative thereof such as a thioester or an ester (e.g. an alkyl ester), an amide, an acid halide (e.g. an acid chloride) or an acid anhydride. A wide variety of reaction conditions may be employed depending upon the nature of the acylating agent, but in general the reactants may be refluxed together preferably in an inert liquid medium such as ether, benzene or toluene.

A most convenient method of synthesis is to react the acid chloride with the appropriate amine. Preferably one equivalent of the halide should be used with two or more equivalents of the amine, but the molar excess of the amine may be replaced by another base such as triethylamine, pyridine, dimethylaniline, anhydrous potassium or sodium carbonate. A wide variety of polar or non-polar liquid media may be used including water, alkanols such as methanol, ethanol, etc., ether, dioxane, benzene, toluene, xylene, petroleum ether, cyclohexane, tetrahydrofuran, chloroform and carbon tetrachloride. A wide range of temperature conditions may be employed, for example from $-10°$ to the reflux temperature of the reaction mixture.

The compounds of formula (I) may be further prepared directly from the corresponding alcohol or aldehyde of formula (III) and (IV) at a temperature below 10° C.

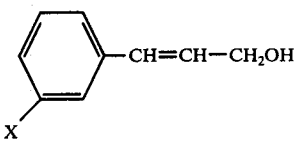 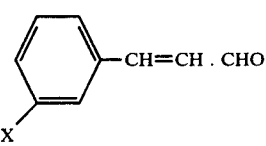

(III) (IV)

wherein X has the meaning in formula (I), by reaction with the appropriate amine $RNH_2$ in the presence of nickel peroxide and an inert liquid medium such as ether, benzene, tetrahydrofuran, or a petroleum hydrocarbon.

The compounds of formula (I) may also be made by the reaction of an amide of formula (V): R.NH.W wherein W is a leaving group, for example —CO.H (a formamide), —CO.alkyl (an amide), —$CONH_2$ (urea), —COO.alkyl (urethane having 1-4 carbon atoms in the alkyl group), with an acid of formula (II) or a reactive derivative thereof, for example the acid anhydride or halide. When the anhydride is used, a catalytic amount of sulphuric acid is preferably included. The reactants are conveniently heated together in a liquid medium.

In a further method for making a compound of formula (I), water, a hydrogen halide or molecular halogen is eliminated from a compound of formula (VI)

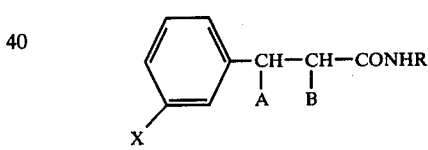

(VI)

wherein A and B are the same and each is halo or one of A and B is halo or hydroxy and the other is hydrogen, and X and R have the meaning given in formula (I) above. For example, the elimination of water from the α- or β-hydroxy compounds of formula (VI) may be effected by reaction with a dehydrating agent such as a base (eg. aqueous sodium hydroxide) or concentrated sulphuric or polyphosphoric acids. The monohalo intermediates may be treated with a base (eg. potassium hydroxide of dimethylaniline) or merely heated to release the hydrogen halide. The dihalo intermediates may be reduced, for example with zinc and ethanol or converted to the diiodo compounds by treatment with potassium iodide with subsequent release of molecular iodine.

The intermediate acids of formula (II) may be made by classical organic synthetic methods such as the Perkin synthesis, the Reformatsky reaction and the Knoevenagel condensation.

The compounds of formula (I) may be used for the treatment or prophylaxis of convulsions of mammals such as mice, dogs and cats and more importantly of man. In particular they may be used in the treatment of epilepsy such as grand mal, petit mal, psychomotor epilepsy and focal seizures at a dose of 2 to 200 mg/kg of body weight per day. The optimum dose of course will vary with the nature of the compound, the condition of the patient and the route of administration, but the preferred dose is in the range of 20 to 60 mg/kg, most conveniently 30 to 50 mg/kg body weight, per day. Administration of the desired daily dose is preferably in three divided doses. For example, convenient forms of administration include tablets each containing from 100 to 500 mg of a compound of formula (I).

For use in medicine the compounds of formula (I) may be administered as a pure chemical but are preferably presented with an acceptable carrier therefor as a pharmaceutical composition. The carrier must of course be 'acceptable' in the sense of being compatible with the other ingredients of the composition and not deleterious to the recipient of the composition. The carrier may be a solid or a liquid or a mixture of solid and liquid substances, and is preferably formulated with a compound of formula (I) as a unit-dose composition, for example a tablet, capsule or sachet for oral administration or a suppository for rectal administration. Other pharmaceutically active substances may also be present in compositions of the present invention, and the composition may be formulated by any of the well-known techniques of pharmacy consisting basically of admixture of its components.

For oral administration, fine powders or granules of the compounds may contain diluents and dispersing and surface active agents, and may be presented in a draught in water or in a syrup; in capsules or cachets in the dry state or in an aqueous or non-aqueous suspension, when a suspending agent may also be included; in tablets, preferably made from granules of the active ingredient with a diluent, by compression with binders and lubricants; or in a suspension in water or a syrup or an oil or in a water/oil emulsion, when flavouring, preserving, suspending, thickening and emulsifying agents may also be included. The granules or the tablets may be coated, and the tablets may be scored.

For parenteral administration (by intramuscular or intraperitoneal injection), the compounds may be presented in unit dose or multi-dose containers in aqueous or non-aqueous injection solutions which may contain antioxidants, buffers, bacteriostats and solutes which render the compounds isotonic with the blood; or in aqueous or non-aqueous suspensions when suspending agents and thickening agents may also be included; extemporaneous injection solutions and suspensions may be made from sterile powders, granules or tablets which may contain diluents, dispersing and surface active agents, binders and lubricants.

It will be understood from the foregoing description that what we will claim in accordance with this invention comprises any novel feature described herein, principally but not exclusively as follows:

a. A compound of the formula (I)

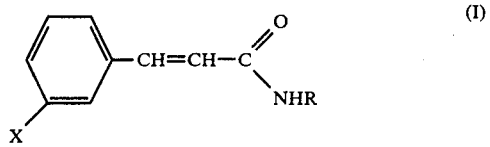

(I)

wherein X is chlorine, bromine or iodine and R is alkyl having 1 to 3 carbon atoms except where X is chlorine and R is hydrogen.

b. A compound of the formula (I) having the trans configuration.

c. 3-Bromo-N-ethylcinnamamide.

d. The synthesis of a compound of formula (I) by any known method and in particular the methods specifically described above and including the reaction of an acid m-X-PhCH = CHCO$_2$H or a reactive derivative thereof with a compound of the formula R.NH.W wherein W is a leaving group and R and X have the meaning in formula (I).

e. A pharmaceutical composition comprising a compound of formula (I) wherein R is hydrogen or alkyl and a pharmaceutically acceptable carrier therefor.

f. A method for the treatment or prophylaxis of convulsions of a mammal comprising the administration to the mammal of an anti-convulsant effective, non-toxic amount of a compound of formula (I) wherein R is hydrogen or alkyl.

The following examples illustrate the invention.

EXAMPLE 1

3-Bromo-N-isopropylcinnamamide

Trans m-bromocinnamic acid (11.4 g) in dry benzene (75 ml) was heated to reflux and then a mixture of thionyl chloride (12 g) in dry benzene (50 ml) was added at such a rate as to maintain constant reflux. The reaction mixture was heated at reflux for an additional 2 hr. after the addition of thionyl chloride. The solvent and excess thionyl chloride were then removed under reduced pressure to give trans 3-bromocinnamoyl chloride (ca. 12.3 g). A solution of the 3-bromocinnamoyl chloride in toluene (150 ml) was added dropwise with stirring to a solution of isopropylamine (10 g) in ether (200 ml). The reaction mixture was stirred at room temperature for 1 hour and then heated at reflux for 1 hour. The solvent and excess amine were removed under reduced pressure. The crude residue was triturated with water, filtered, and recrystallized from ethanol-water to give white, crystalline trans 3-bromo-N-isopropylcinnamamide, m.p. 85°-86° C. Elemental analysis, NMR and IR spectra all confirmed the identity of the product.

EXAMPLE 2

3-Bromo-N-ethylcinnamamide

A solution of trans 3-bromocinnamoyl chloride (12.3 g) in anhydrous toulene (150 ml) was added slowly with stirring to a solution of ethylamine (10 g) in dry ether (100 ml) at room temperature. The reaction mixture was heated at reflux for 1 hour, and the solvent and excess amine were then removed under reduced pressure. The residue was triturated with water, filtered, and recrystallized from ethanol-water to give trans 3-bromo-N-ethylcinnamamide, m.p. 89°-90° C., as a white crystalline material. NMR and IR spectra as well as elemental analysis were consistent with the assigned structure.

EXAMPLE 3

3-Bromo-N-ethylcinnamamide

Trans m-bromocinnamic acid (14.8 g), ethanol (173 ml) and concentrated sulfuric acid (0.4 ml) were combined and heated at reflux for 15 hours. About 150 ml of the ethanol was distilled off, and the remaining solution was poured into ice/water (140 ml). The cold mixture was made strongly alkaline with 40% sodium hydroxide and extracted with methylene chloride (4 × 60 ml). The combined methylene chloride extract was dried over anhydrous potassium carbonate. The potassium carbonate was removed by filtration and the solvent stripped off under reduced pressure. Trans ethyl 3-bromocinnamate, was obtained as a partially solidified oil. (IR spectrum was consistent with this compound).

Trans ethyl 3-bromocinnamate (8.4 g), ethylamine (6.7 g), methanol (18 ml) and 4A molecular sieves (1 g) were combined and heated at reflux for ½ hour. The mixture was cooled to about 45° C and sodium methylate (0.6 g) added. The mixture was then heated at reflux 1½ hour and then cooled. It was acidified with concentrated hydrochloric acid (12 ml). The sieves were removed by filtration. Ice water was added to the filtrate to precipitate trans 3-bromo-N-ethylcinnamamide, m.p. 89°–90° C (after recrystallization from ethanol/water).

EXAMPLE 4

3-Bromo-N-methylcinnamamide

A solution of trans 3-bromocinnamoyl chloride (5 g) in dry benzene (100 ml) was added with stirring to an ethereal (200 ml) solution of methylamine (3 g). After the addition was complete, a slow stream of methylamine gas was bubbled through the reaction mixture at room temperature for 1 hour. Solvent and excess amine were removed under reduced pressure. The crude product was triturated with water, filtered, and recrystallized from ethanol-water to give trans 3-bromo-N-methylcinnamamide, m.p. 147°–147.5° C. NMR, IR, and elemental analysis were consistent with this structure.

EXAMPLE 5

3-Chloro-N-ethylcinnamamide

Trans 3-chlorocinnamoyl chloride (4.4 g) in dry benzene (75 ml) was allowed to react with an excess of ethylamine in dry ether (75 ml) according to the procedure of Example 2. Trans 3-chloro-N-ethylcinnamamide, m.p. 87°–88° C, was obtained which had NMR, IR, and elemental analysis consistent with this structure.

EXAMPLE 5(a)

3-Iodo-N-ethylcinnamamide

Trans m-iodocinnamoyl chloride was prepared from trans m-iodocinnamic acid according to the standard procedure exemplified in Example 1. The acid chloride (6.6g) in dry toluene (200ml) was added with stirring to a solution of ethylamine (3.0g) in dry ether (300ml) at room temperature. The reaction mixture was heated at reflux for 1 hour and then worked up according to Example 2 to yield trans m-iodo-N-ethylcinnamamide (6.4g, 93% of theoretical), m.p. 116°–117° C as a white, crystalline material. NMR, IR and elemental analysis were consistent with this structure.

EXAMPLES 6-10

Following the procedure of Example 2, the following trans compounds were prepared (in all cases the NMR and IR spectra and elemental analysis confirmed the structure) in which X and R have the values in formula (I):

| Example | X | R | m.p. (° C) |
|---|---|---|---|
| 6 | Cl | CH$_3$ | 124 – 125 |
| 7 | Cl | CH$_2$CH$_2$CH$_3$ | 78 – 79 |
| 8 | Br | CH$_2$CH$_2$CH$_3$ | 84 – 85 |
| 9 | Br | H | 107 – 108 |
| 10 | Cl | H | 81 – 82 |

EXAMPLE 11

A suppository was formulated from the following ingredients:

| trans | 3-Bromo-N-ethylcinnamamide | 300 mg |
|---|---|---|
| | Cocoa butter | 2000 mg |

EXAMPLE 12

A soft gelatin capsule was filled with the following ingredients:

| trans | 3-Bromo-N-ethylcinnamamide | 300 mg |
|---|---|---|
| | Lactose | 75 mg |
| | Starch, corn | 20 mg |
| | Fused silica | 2 mg |
| | Magnesium stearate | 3 mg |

EXAMPLE 13

A syrup suspension was prepared from the following ingredients:

| trans | 3-Bromo-N-ethylcinnamamide | 300 mg |
|---|---|---|
| | Sodium carboxymethylcellulose | 20 mg |
| | Microcrystalline cellulose | 100 mg |
| | Glycerin | 500 mg |
| | Polysorbate 80 | 10 mg |
| | Flavouring agent | Q.S. |
| | Preserving agent | .1% |
| | Sucrose syrup | Q.S. to 5 ml |

EXAMPLE 14

A compressed tablet was prepared from the following:

| trans | 3-Bromo-N-ethylcinnamamide | 300 mg |
|---|---|---|
| | Corn starch | 50 mg |
| | Microcrystalline cellulose | 50 mg |
| | Stearic acid | 4 mg |
| | Magnesium stearate | 1 mg |
| | Fused silica | 1 mg |

EXAMPLE 15

In the MES pharmacological test referred to hereinbefore, trans 3-bromo-N-ethylcinnamamide had an oral ED$_{50}$ in the mouse and rat of 80 mg/kg and 26 mg/kg respectively.

EXAMPLE 16

Anticonvulsant activity was determined in mice using the Maximal Electroshock Test (MES) performed according to the method of Woodbury and Davenport, supra- with corneal electrodes and a Wahlquist Electroshock Stimulator Model E (manufactured by Wahlquist Instrument Co., Salt Lake City, Utah.)

trans 3-Bromo-N-ethylcinnamamide was suspended in 0.5 % aqueous methylcellulose by homogenation in a tissue homogenization grinder to give a particle size such that greater than 51% was less than 5 microns and greater than 87% was less than 20 microns to give concentrations of 5, 7.5, 10, 15, and 20 mg of compound per ml of methylcellulose solution. The mice, male, ICR Blue Spruce of 22g. average weight, were divided into six groups of ten mice each. The trans 3-Bromo-N-ethyl-cinnamamide suspensions were administered 1 hour prior to test orally (p.o.) by direct injection into the stomachs of the mice. The control mice received an equivalent volume of p.o. aqueous 0.57. methylcellulose one hour prior to test.

A current of 50 ma was applied to the cornea of the mice for 0.2 second and the time elapsed between application of the electric shock and hind limb extensor seizure (convulsive extension of the hind legs) measured and recorded as latency of hind limb extension. Animals were considered protected (p) if the hind limb extensor component of the convulsion was blocked. An increase over the control group in mean latencies is also indicative of anti-convulsant activity.

| Dose, mg/kg Mice in Group | Latency of Hind Limb Extension (seconds) | | | | | |
|---|---|---|---|---|---|---|
| | 0 (control) Group 1 | 50 Group 2 | 75 Group 3 | 100 Group 4 | 150 Group 5 | 200 Group 6 |
| 1 | 1.8 | p | p | 1.2 | p | p |
| 2 | 2.0 | p | 2.8 | 4.8 | p | p |
| 3 | 1.5 | 1.8 | 3.3 | p | p | p |
| 4 | 1.8 | 1.8 | 2.1 | 2.2 | p | p |
| 5 | 1.2 | 1.2 | 3.2 | p | p | p |
| 6 | 1.2 | 1.2 | p | p | p | p |
| 7 | 1.2 | p | 1.8 | 1.8 | p | p |
| 8 | 1.8 | 1.2 | 2.8 | p | p | p |
| 9 | 1.8 | 1.2 | p | p | p | p |
| 10 | 1.8 | 2.2 | p | 1.5 | p | p |
| % protected | 0 | 30 | 40 | 50 | 100 | 100 |
| Mean Latency | 1.61 | 1.51 | 2.66 | 2.30 | — | — |

The above test results (% protected) demonstrates that trans 3-Bromo-N-ethylcinnamamide is effective in preventing convulsive hind limb extension due to electrical shock in mice.

Each group comprised 10 mice. A different group was used for each dosage. p indicates protected against electrical shock.

What we claim is:
1. The compound trans 3-iodocinnamamide.
2. Trans 3 - Bromo - N - ethylcinnamamide.
3. The trans compound of formula I

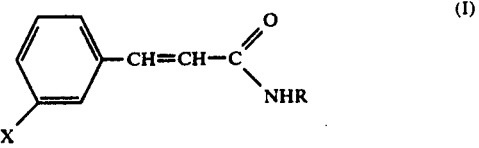

where X is iodo and R is alkyl having 1 to 3 carbons.
4. The compound 3-iodo-N-ethylcinnamamide.
5. The compound of claim 3 where X is iodo and R is isopropyl.
6. The compound of claim 3 where R has 2 to 3 carbons.